(12) United States Patent
Rymut et al.

(10) Patent No.: US 6,517,497 B2
(45) Date of Patent: Feb. 11, 2003

(54) METHOD AND APPARATUS FOR MONITORING RESPIRATION USING SIGNALS FROM A PIEZOELECTRIC SENSOR MOUNTED ON A SUBSTRATE

(75) Inventors: Russell Rymut, Milwaukee, WI (US); Eric Slotty, Waukesha, WI (US); Narendra Kini, Delafield, WI (US)

(73) Assignee: GE Medical Systems Information Technologies, Inc., Waukesha, WI (US)

( * ) Notice: Subject to any disclaimer, the term of this patent is extended or adjusted under 35 U.S.C. 154(b) by 0 days.

(21) Appl. No.: 09/735,843

(22) Filed: Dec. 13, 2000

(65) Prior Publication Data

US 2002/0072685 A1 Jun. 13, 2002

(51) Int. Cl.⁷ .............................................. A61B 5/113

(52) U.S. Cl. ...................... 600/538; 600/586; 600/533; 600/532; 600/534

(58) Field of Search ................................ 600/586, 538, 600/533, 532, 534

(56) References Cited

U.S. PATENT DOCUMENTS

| | | | | |
|---|---|---|---|---|
| 4,443,730 A | * | 4/1984 | Kitamura et al. | 310/330 |
| 5,235,989 A | | 8/1993 | Zomer | |
| 5,353,793 A | * | 10/1994 | Bornn | 128/642 |
| 6,290,654 B1 | * | 9/2001 | Karakasoglu | 128/201.23 |
| 6,375,621 B1 | | 4/2002 | Sullivan | |
| 2001/0047127 A1 | * | 11/2001 | New et al. | 600/300 |

* cited by examiner

*Primary Examiner*—Charles G. Freay
*Assistant Examiner*—Emmanuel Sayoc
(74) *Attorney, Agent, or Firm*—Michael Best & Friedrich LLP

(57) ABSTRACT

A method and apparatus for monitoring and/or quantitatively measuring a patient's respiration using a flexible piezoelectric film sensor. The apparatus includes a piezoelectric film which converts acoustical waves generated by the patient's respiration into electrical signals. The piezoelectric film sensor can be used to monitor the respiration of a patient by correlating the sound generated in the patient's airway with respiratory activity. Further, the data generated by the sensor may be further analyzed by a patient monitor to diagnose respiratory conditions.

32 Claims, 5 Drawing Sheets

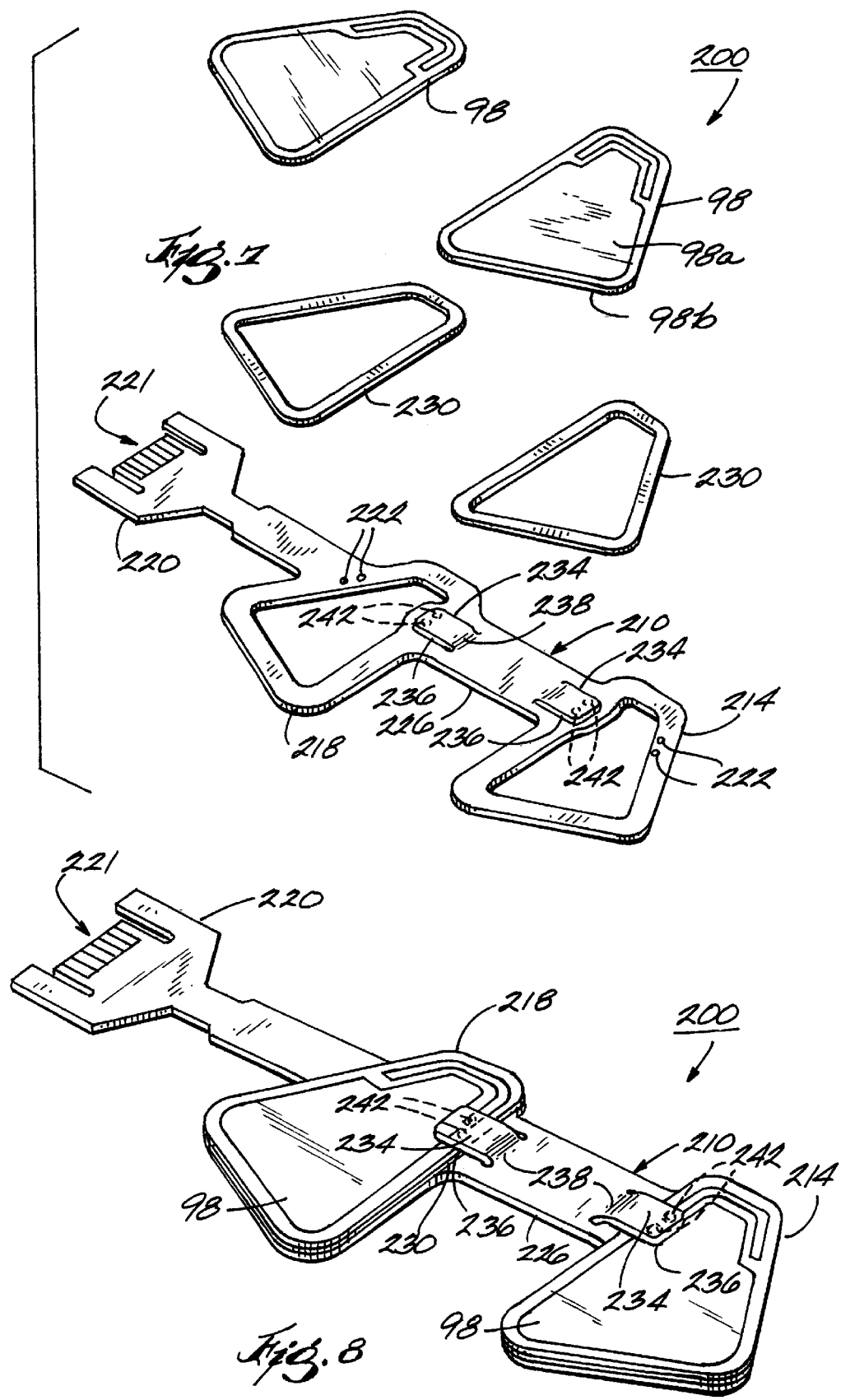

METHOD AND APPARATUS FOR MONITORING RESPIRATION USING SIGNALS FROM A PIEZOELECTRIC SENSOR MOUNTED ON A SUBSTRATE

BACKGROUND OF THE INVENTION

The present invention relates to a method and apparatus for monitoring and/or quantitatively measuring the respiration of a patient and, particularly, to a method and apparatus for monitoring a patient's respiration using a flexible piezoelectric film sensor.

Electro-mechanical devices may be used to measure the physiological characteristics of a subject for monitoring particular physical characteristics and diagnosing the subject's health. Respiration monitors which seek to quantify a patient's breathing are one category of patient monitoring device. In conventional hospital respiration monitors, a patient's breathing is monitored by a technique known as impedance pneumography. Electrodes are placed on the patient's chest and trans-thoracic electrical impedance is measured with a small high-frequency current. As the patient breaths, air fills the lungs resulting in a change to the chest's electrical impedance. An impedance pneumograph measures this impedance variation/modulation in order to determine the respiratory status of the patient. This technique, while widely used in clinical environments, suffers from several major limitations. First, the technique is fundamentally a measure of impedance changes related to chest motion. Therefore any patient motion, whether due to respiration or other movements, will cause a modulation in the impedance signal. Such non-respiratory modulations are referred to as artifacts. These artifacts often contribute to erroneous calculation of respiration rate, false alarms, and undetected cessation of breathing (also known as apnea).

Second, the impedance pneumography technique monitors respiratory effort, but does not measure actual respiratory airflow. In certain patients, a blockage of the airway may restrict the amount of air entering the lungs (obstructive apnea), but because the chest wall continues to move (as the patient attempts to breathe) impedance pneumograph respiratory monitors will not indicate any abnormal breathing patterns. The inability of impedance pneumography to detect obstructive apnea is a severe limitation of the technique in a clinical setting.

Alternatively, respiration can be monitored through a device using one or more thermistors. Thermistors are resistors made of semiconductors having resistance that varies rapidly and predictably with temperature. The thermistors detect respiration by measuring temperature changes in air temperature directly adjacent to a patient's airflow. Normally such devices include portions which cover one or more nostril or the patient's mouth. As such, thermistors can impede a patient's natural breathing and do not accurately measure respiration.

Other existing respiration monitors directly measure inspired and expired air through measurement of air flow using one or more air flow transducers. In such existing patient monitors, bi-directional air flow passing one end of a tube induces unidirectional air flow at the other end which is detected by a transducer to provide output signals corresponding to the movement of air. Like thermistors, however, such an arrangement can impede the patient's breathing and is not adaptable for use as a diagnostic tool for respiratory conditions.

SUMMARY OF THE INVENTION

Accordingly, there is a need for improved methods and apparatus for monitoring a patient's respiration that quantitatively measure respiration, are resistant to artifact interference, suitable for use as a diagnostic tool and which do not suffer from the drawbacks associated with existing respiration monitors.

The present invention provides a method and apparatus for monitoring a patient's respiration which uses a sensor placed on the surface of a patient's neck to measure sound waves generated by respiratory airflow to monitor and/or quantitatively measure the respiration of a subject. Specifically, the present invention utilizes piezoelectric film (piezo film) placed on a patient's neck as a respiratory sensor.

The invention is manufactured using a piezoelectric film (utilizing the piezoelectric effect) arranged and configured to perceive acoustic waves associated with respiration while eliminating non-respiratory sound artifacts. Voltage is produced between opposite surfaces of the piezo film when mechanical forces are applied. As such, the piezoelectric effect converts mechanical acoustical energy into electrical energy. Piezo film has several beneficial characteristics when used as a sensing element. First, piezo film is thin, flexible and light, providing a comfortable, yet tightly coupled interface to the patient which does not inhibit natural respiration. Second, respiration monitors based on the present invention are relatively inexpensive, allowing the sensor to be disposable or semi-disposable. Third, piezo film sensors are passive devices, which allow the present invention to function without subjecting the patient to electrical excitation. Finally, the sensor's acoustic impedance is well matched to tissue, allowing maximum signal transfer from the skin to the sensor while simultaneously rejecting external acoustic vibrations that reach the sensor through the air.

Preferably, the sensor is coupled to a device such as a patient monitor which acts as a signal acquisition unit accepting signals generated by the sensor, processes the signals and correlates the signals over time to determine one or more physiological characteristics associated with respiration.

An advantage of the method and apparatus described is that respiration of a patient may be monitored using an inexpensive sensor which is comfortable for the patient and suitable for monitoring or quantitatively measuring a wide range of respiratory characteristics.

An additional advantage of the present invention is that the device may be used to diagnose various respiratory conditions. Information contained in breath sounds may be used in new monitoring applications such as correlating the signature of the sound produced by a patient's respiration to detect the presence of fluid collection in the lungs or detecting respiratory failure. As such, the present invention also provides a method and apparatus for diagnosing medical conditions associated with respiration, including, but not limited to apnea, the collection of fluid in a patient's lungs and respiratory failure. Preferably, the sensor is coupled to a device which accepts signals generated by the sensor and analyzes the signals in comparison to respiratory auditory characteristics associated with known respiratory conditions.

Yet another advantage of the invention is that the present invention could be configured and adapted for use in other human air or fluid passage-ways, such as arteries or veins or, alternatively, on mechanical devices with air or fluid flow such as mechanical conduits or pipelines.

Other features and advantages of the present invention will become apparent by consideration of the detailed description and accompanying drawings.

BRIEF DESCRIPTION OF THE DRAWINGS

FIG. 7 is an exploded perspective view of another apparatus embodying the invention.

FIG. 8 is a perspective view of the apparatus shown in FIG. 7.

DETAILED DESCRIPTION

Figure 1:
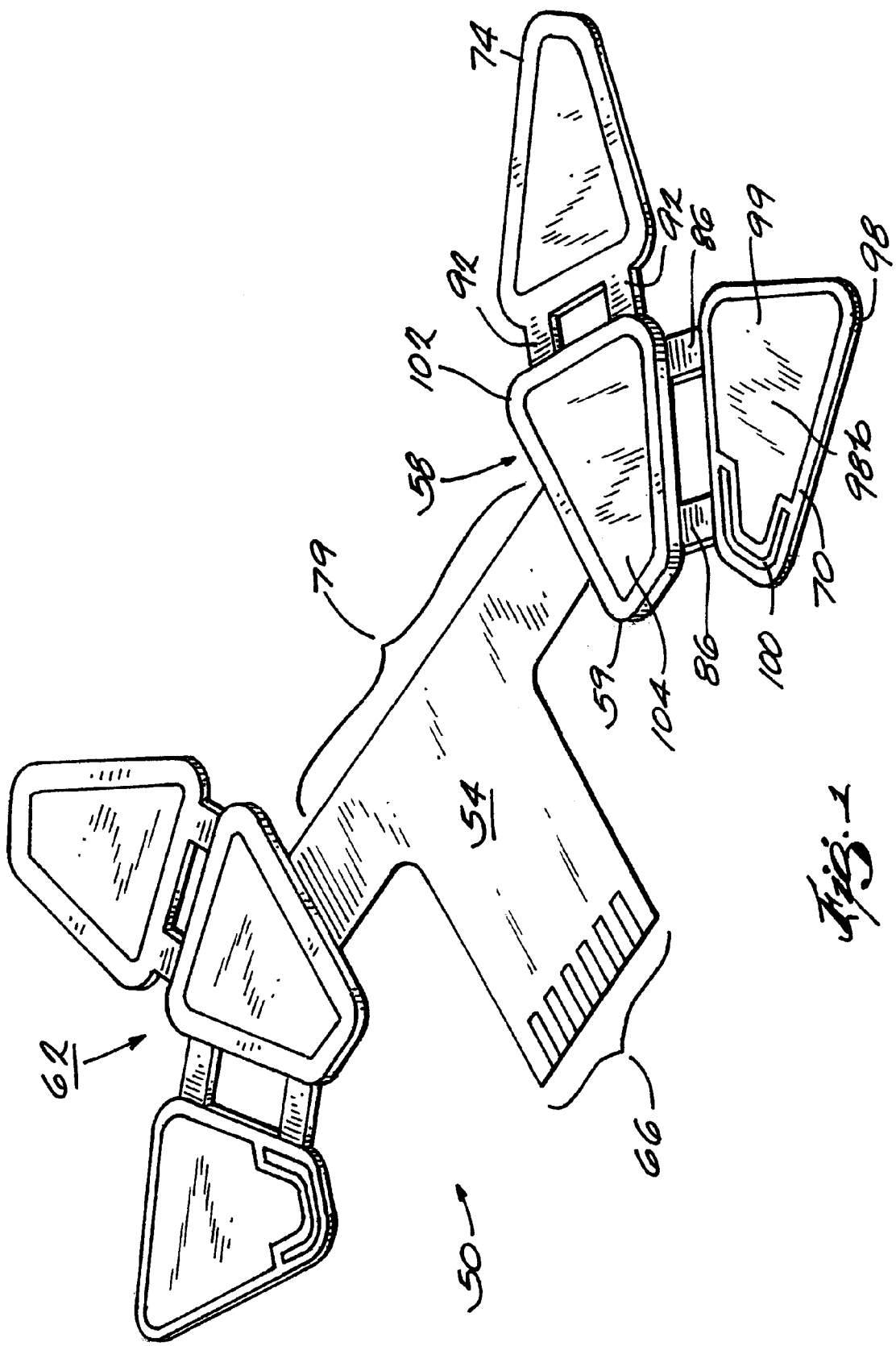
FIG. 1 is a perspective view of a partially assembled apparatus embodying the invention.

Before one embodiment of the invention is explained in detail, it is to be understood that the invention is not limited in its application to the details of the construction and the arrangements of the components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

As seen in FIG. 1, the apparatus 50 embodying the invention includes a flexible substrate 54. The flexible substrate 54 includes a circuit layer 56 (FIG. 2) and a backing layer 57 (FIG. 3).

As further shown in FIG. 1, substrate 54 includes a first sensing region 58, second sensing region 62 and a connecting portion 79 connecting the first and second sensing regions 58, 62 to a patient monitor interface 66. The patient monitor interface 66 includes electrical contacts 120, 122. As shown in the drawings, the first and second sensing regions 58, 62 are identical mirror images of one another. Accordingly, only first sensing region 58 will be described in detail.

First sensing region 58 has a base portion 59, film ear 70 and contact ear 74. Film ear 70 and contact ear 74 are trapezoidal rings integrally formed with (as a part of) the flexible substrate 54, are shaped to conform to base portion 59, and are connected to flexible substrate 54 via "living" (or "integral") substrate hinges 86 and 92, respectively.

Figure 2:
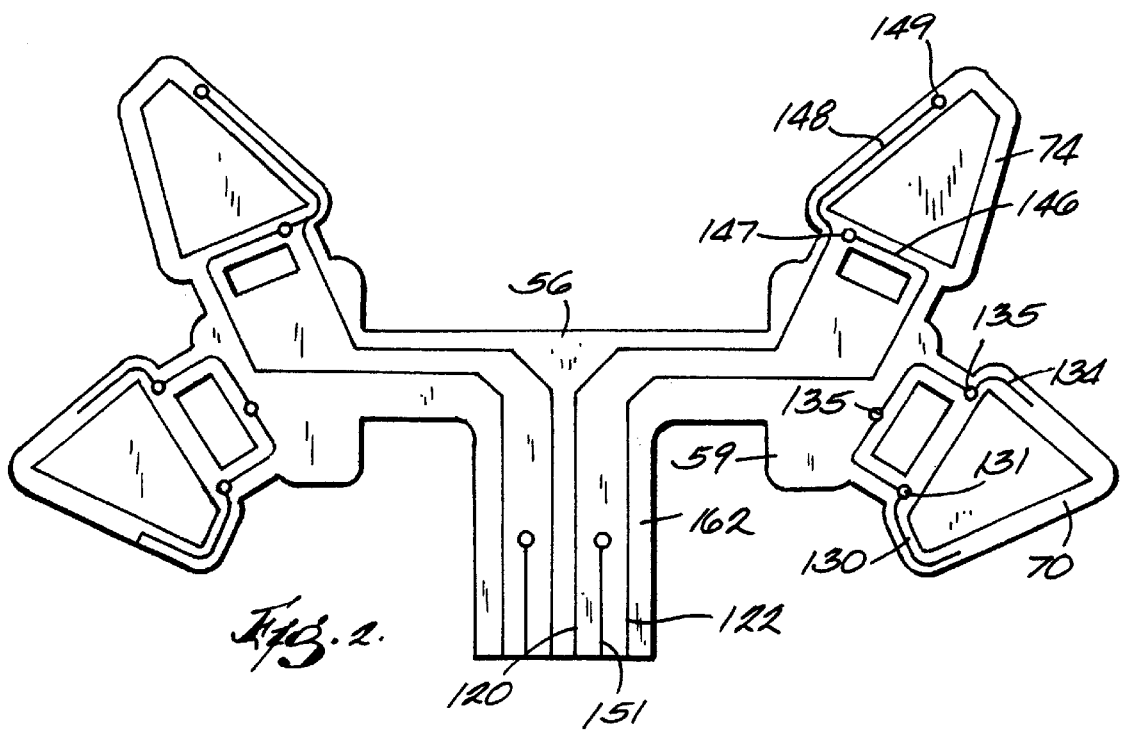
FIG. 2 is a front planar view of the flexible circuit layer of the substrate depicted in FIG. 1 without the piezo film attached.
Figure 3:
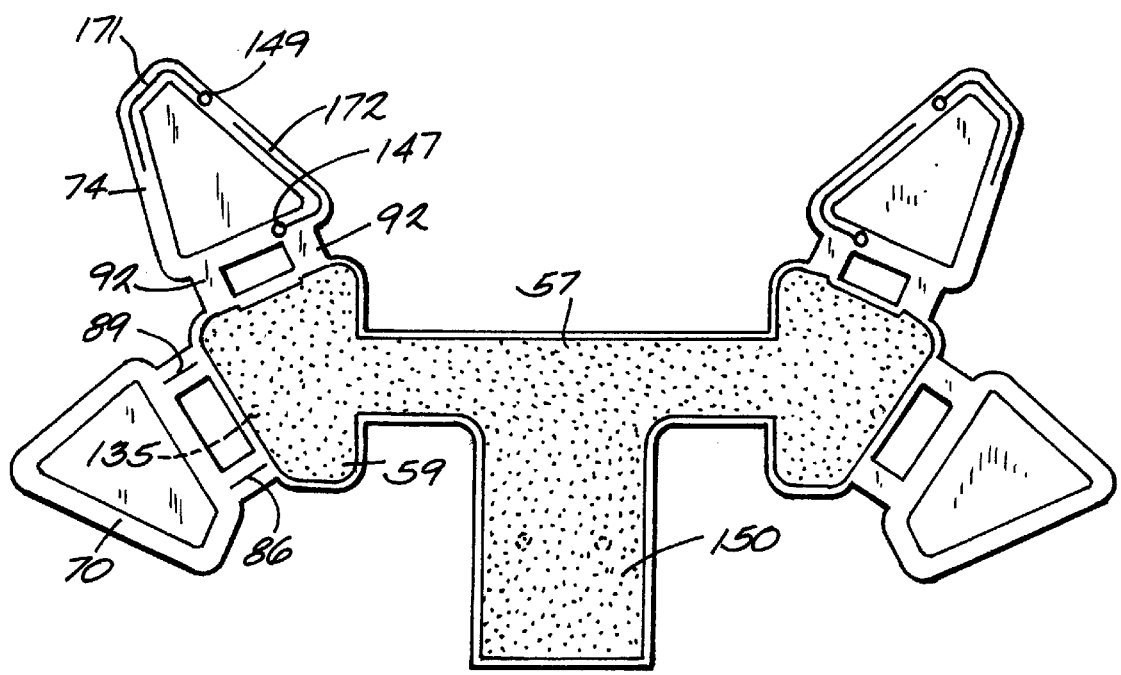
FIG. 3 is a back planar view of the backing layer of the substrate depicted in FIG. 2.

As shown in FIG. 2, the circuit layer 56 includes circuit contacts 146 and 148 found on contact ear 74 and electrically connected to contacts 122 and 120, respectively. Circuit contacts 146, 148 include feed-through contacts 147, 149, respectively, which provide an electrical feed-through to the backing layer 57. The circuit layer also includes circuit contacts 130 and 134. Circuit contacts 130 and 134 are electrically connected at feed-through contact 135, which provides an electrical feed-through to the backing layer 57. The circuit layer 56 also includes contact 151 which provides electrical feed-through to backing layer 57.

The backing layer 57 includes circuit contacts 171 and 172 which connect to circuit contacts 148 and 146, respectively, via feed-through contacts 149 and 147, respectively. The backing layer 57 also includes an electrically conductive reference layer 150 which acts as a radio frequency (RF) interference shield. The reference layer 150 is electrically connected to circuit contacts 130 and 134 via feed-through contact 135, and to contact 151 via feed-through contact 162.

As further shown in FIG. 1, apparatus 50 includes a trapezoidal piezo film 98 mounted on film ear 70 and shaped to conform to film ear 70. Trapezoidal piezo film layer 98 has a top 98a (FIG. 4 only) and bottom 98b (FIG. 1). Trapezoidal piezo film layer 98 also includes a sensing portion 99 and a reference portion 100 electrically isolated from the sensing portion 99. The piezo film 98 is constructed from a thin sheet of processed polyvinylidene fluoride. When subjected to mechanical stress or strain, piezo film 98 generates a charge on the outer surfaces 98a (FIG. 4 only) and 98b (FIG. 1) at both the sensing portion 99 and the reference portion 100. The charge creates a voltage potential across the portions 99 and 100 of top surface 98a and bottom surface 98b.

Figure 5:
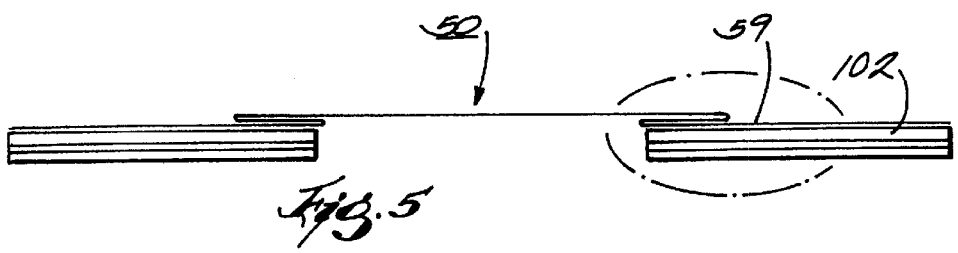
FIG. 5 is partially cut-away side planar view of the apparatus embodying the invention taken along line 5—5 in FIG. 4.
Figure 5A:
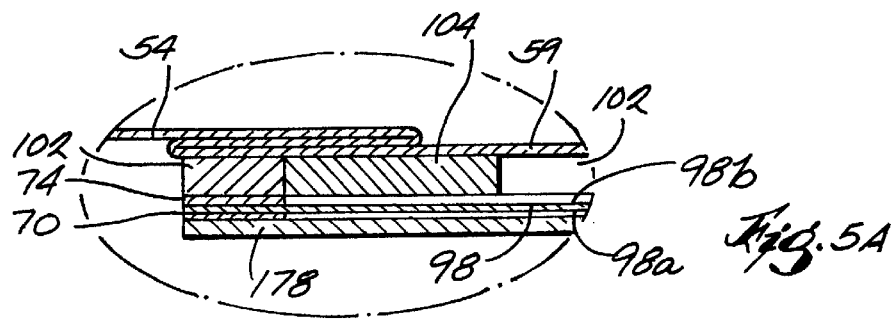
FIG. 5A is an enlarged side planar view of the circled portion of the apparatus depicted in FIG. 5.

As shown in FIGS. 5 and 5A, first sensing region 58 also includes a rigid base ring 102 connected to base portion 59, and trapezoidal first foam material 104 mounted on base portion 59 inside of base ring 102. The base ring 102 and foam material 104 are attached to the base portion 59 using any appropriate means. In the embodiment shown in the drawings, the base ring 102 and foam material 104 are attached to base portion 59 using a medically acceptable adhesive (not shown).

As shown in FIG. 1, first sensing region 58 of apparatus 50 is assembled by folding contact ear 74 over base portion 59, base ring 102 and foam material 104. Film ear 70 (including piezo film 98) is then folded over contact ear 74 providing a layered disposition of base portion 59, contact ear 74 and film ear 70 about the periphery of the sensing region 58, and also a layered disposition of base portion 59, foam material 104 and piezo film 98 in the interior of the sensing region 58.

Adhesion between each of the layered sections is achieved using an electrically conductive adhesive such as 3M Tape No. 9703 (Electrically Conductive Adhesive Transfer Tape) (not shown) which conducts charge from the piezo film 98 only in the "Z" direction, i.e., through the thickness of the material. Use of such an adhesive ensures electrical contact between the piezo film 98 and flex circuit 54 to conduct charges generated on the surfaces of the piezo film 98a and 98b as described below and depicted in FIG. 5.

Figure 6:
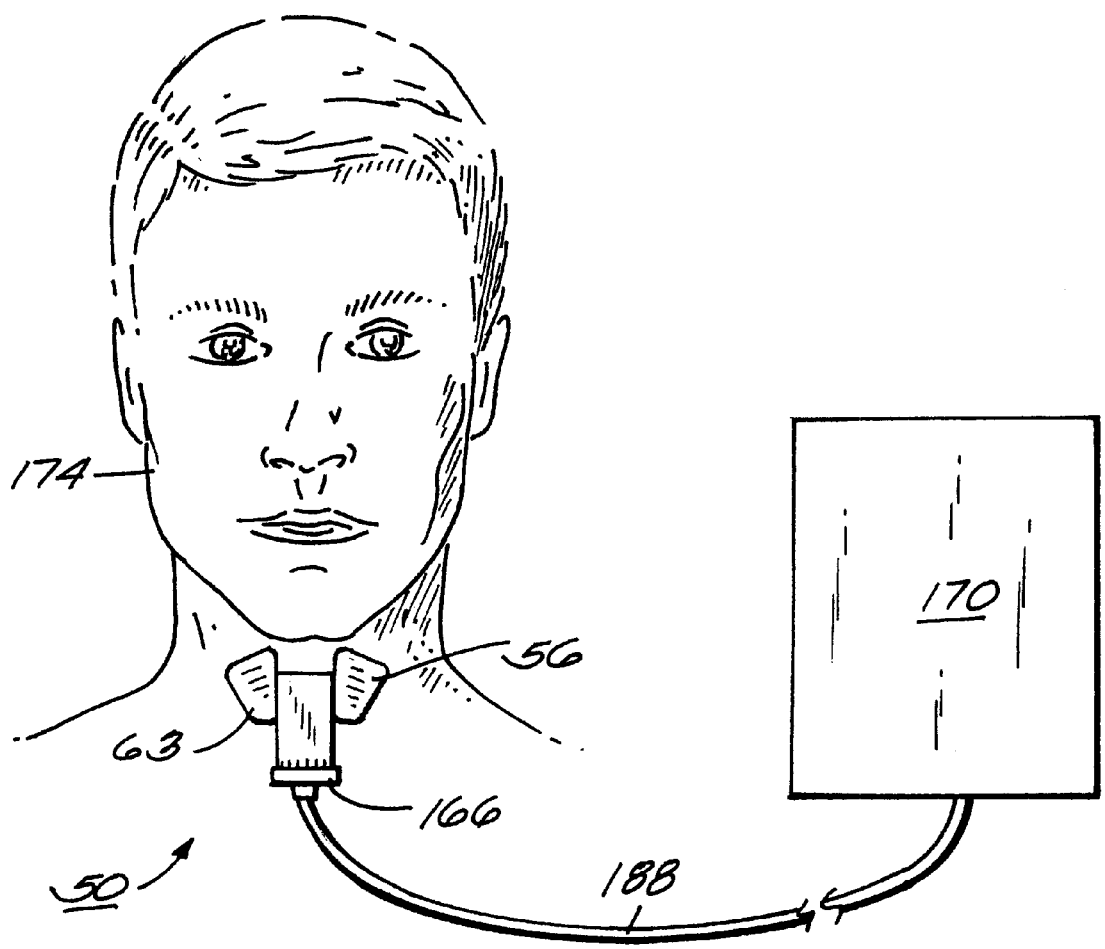
FIG. 6 is an illustration of the proper placement of the apparatus depicted in FIG. 4 on a patient including a patient monitor embodying the invention.

Referring to FIG. 2, exposed electrical conductors 120, 122 on the patient monitoring interface region 66 of the flexible circuit 56 conduct charge from corresponding piezo film metal contacts 171 and 172, through corresponding feed-through contacts 149, 147 to circuit contacts 148, 146 and therefrom to patient monitor signal acquisition unit 170 (as shown in FIG. 6). A connector 166 is attached at the patient monitor interface 66 to exposed electrical conductors 120, 122 in order to allow for quick connection or disconnection to a patient monitor signal acquisition unit 170 (also shown in FIG. 6). While contact 162 is shown connected to reference layer 150, in other embodiments, contact 162 may be used for additional electrical features such as to detect whether the sensor is attached to the patient monitor.

Figure 4:
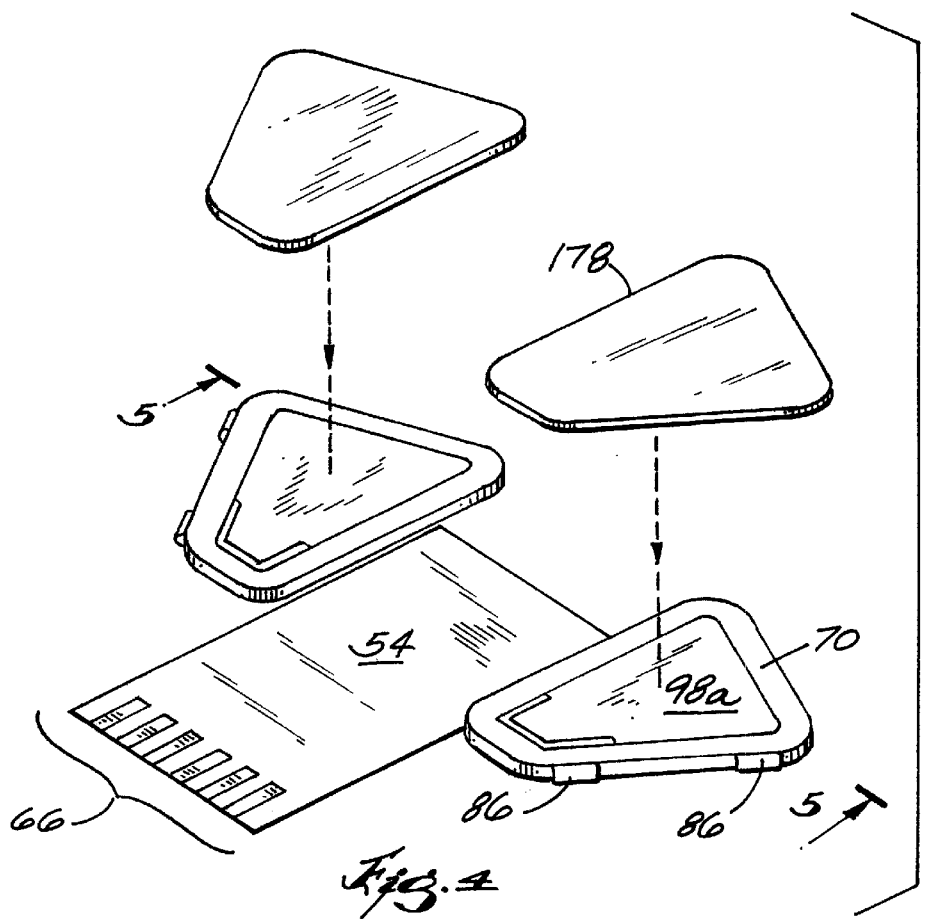
FIG. 4 is a perspective view of a fully assembled apparatus embodying the invention as seen in FIG. 1 prior to application of an adhesive material.

As seen in FIG. 6, the apparatus 50 is affixed to a patient and operatively connected to a patient monitor acquisition unit 170. The apparatus 50 is attached to a patient 174 using two methods. As seen in FIG. 4, first an adhesive hydrogel 178 is used to adhere the first sensing region 58 and second sensing region 62 to the patient. Hydrogel 178 provides a small amount of adhesion strength and serves as an acoustic coupling layer between the skin and sensor 50 by ensuring that there are no air gaps between sensory regions 58, 62 and the patient 174 that could affect the acoustic impedance. In addition to the hydrogel 178, standard medical grade foam tape 184 (not shown), provides additional mechanical attachment strength to prevent movement of the apparatus 50 with respect to the skin. In a preferred embodiment, the tape 184 is configured to assist in establishing the location and proper tension when applying the apparatus 50 to the patient.

As shown in FIG. 6, the apparatus 50 is connected to a patient monitor signal acquisition unit 170. Patient monitor acquisition unit 170 may be any compatible patient monitor signal acquisition unit 170 used in the art or a patient monitor specifically designed for use with apparatus 50. Amplifying electronics in the patient monitor signal acquisition unit 170 are then connected to the patient monitor interface 66 via a connector 166 and cable 188 in order to provide a measurable signal corresponding to the signal induced in the piezo film layer 98 (shown in FIG. 1) to the patient monitor signal acquisition unit 170. In particular, the patient monitor signal acquisition unit 170 may be configured as a monitoring apparatus by qualitatively recording and measuring a subject's respiration over time to determine the patient's breath rate or other physiological characteristic associated with breathing and assist the physician in interpreting the patient's health. Additionally, the patient monitor depicted in FIG. 6 may be configured as a diagnostic apparatus by qualitatively recording a patient's respiration and comparing the patient's respiration to predetermined signals which may indicate one or more medical conditions. Specifically, the apparatus 50 may be used in conjunction with conventional electronic amplifiers and processing algorithms (not shown) to determine the patient's respiration rate, detect both central and obstructive apnea, and diagnose various respiratory disorders.

In use, agitated or disturbed airflow in the airway of the patient 174 provided during inhalation and exhalation causes acoustic pressure waves (sound) to be generated as a patient 174 breathes. As illustrated in FIG. 6, the apparatus 50 is affixed to the patient's neck and measures these sound waves through the tissue of the patient in order to determine respiratory status. The acoustic pressure waves generated in the airway act on the first sensing region 58 causing piezoelectric film layer 98 to flex. This flexion generates charge that may be converted to a signal and subsequently processed by patient monitor signal acquisition unit 170.

The inclusion of foam material 104 between base portion 59 and piezo film 98 (shown in FIG. 1) enhances the acoustic sensitivity of piezo film 98. When assembled, the convex radius of the foam improves sensitivity of first sensing region 58 by transferring mechanical acoustical forces to the most active axis of the piezo film 98. Piezo film 98 is most sensitive when forces are applied along its length (as opposed to through its thickness). Through the curvature of foam material 104, acoustic pressure waves perpendicular to the surface of piezo film 98 that would normally cause little or no longitudinal force to be exerted are directed along the length of piezo film 98 allowing the acoustical forces to induce maximal charge. The foam material 104 has been shown to provide sufficient curvature to achieve an increase in piezo film 98 sensitivity through the passive amplification technique described above. Foam material 104 has the additional benefits of isolating the piezo film 98 from external acoustical vibrations and ensuring that the piezo film layers 98 stay tightly within the apparatus 50 once fully assembled (as seen in FIGS. 4 and 5).

As seen in FIG. 6, the apparatus 50 is configured and arranged in such a manner as to allow for placement on the patient 174 in a position which maximizes the transfer of respiratory sounds. Specifically, the anatomy of the human neck provides two triangular regions on each side of the midline of the larynx. First sensing region 58 and second sensing region 62 are shaped to match these triangular anatomical features for placement on the skin over these regions. The inventors believe that matching the shape of the sensing regions to fit these regions creates better transmission of the acoustical vibrations to the sensor. As these anatomical features vary among the population, the inventors contemplate configuring and dimensioning individual sets of sensors as required to adapt to the dimensional and physiological requirements of the entire population.

The patient monitor signal acquisition unit 170 includes an adaptive noise canceling filter. Specifically, noise reference 100 is connected to feed-through contact 120. Noise reference 100 is arranged and configured to measure mechanically coupled artifacts and is shielded from the pressure waves associated with the patient's 174 respiration. Signals received by noise reference 100 are sampled independently of the breath sound signals and used in an adaptive noise canceling algorithm to alleviate mechanically coupled interference and improve the reliability of the present invention. Noise reference 100 thereby minimizes any pressure wave interference induced in the sensor from any solid part of the present invention (such as when the patient cable 188 drops from some distance).

A method of monitoring the respiration of the patient involves placing the sensor apparatus 50 on the neck surface of the subject and actively monitoring the acoustical vibrations produced by the agitated airflow within the neck of the patient 174 through the sensor 50. The sensor apparatus 50 described above may alternatively be used within a method of diagnosing a respiratory condition by placing the sensor apparatus 50 on the neck of the subject, actively monitoring the acoustical vibrations produced by the agitated airflow within the neck of the patient 174 through the sensor apparatus 50 and comparing the signal generated within the sensor 50 with acoustical signatures which indicate a respiratory condition.

Alternatively, a low-power wireless interface may be included to eliminate the cable 188 that connects the sensor apparatus to the patient monitor signal acquisition unit 174 such as a low power radio-frequency transmitter. This wireless interface may be beneficial to an intensive-care environment where cable clutter is a problem, or where the patient's activity level does not allow for a wired respiration monitor.

FIGS. 7 and 8 illustrate a sensor 200 that is another embodiment of the invention. Like parts are identified using like reference numerals. The sensor 200 includes a flexible substrate 210. The flexible substrate 210 includes a circuit layer (not shown) and the backing layer (not shown). First and second sensing portions 214 and 218 also include electrical contacts 222 mounted on the surface of the flexible substrate 210. The flexible substrate 210 includes a first sensing region 214, second sensing region 218 connected to sensing region 214 by connecting portion 226, and a patient monitor interface 220 connected to sensing portion 218. The patient monitor interface 220 includes electrical contacts 221 for connecting the sensor to a patient monitor 170 as shown in FIG. 6. Each sensing region includes a piezo film 98 mounted thereon using an electrically conductive adhesive 230. The piezo film 98 has a top surface 98a and a bottom surface 98b. The bottom surface 98b is in electrical contact with electrical contacts 222 on the flexible substrate 210. Electrical contacts 222 are connected via electrical conductors (not shown) in flexible substrate 210 to respective electrical contacts 221 on the patient monitor interface 220. While any suitable adhesive can be used, the adhesive shown in the drawings is 3M Tape No. 9703 (Electrically Conductive Adhesive Transfer Tape). As with the apparatus 50, the electrically conductive adhesive conducts charge from the peizo film 98 only in the "z" direction, i.e., through the thickness of the tape.

The connector portion includes a pair of oppositely facing tabs 234 connected to the connector portion 226 via living hinges 238. The tabs 234 also include an underside 236, and electrical contacts 242 on the underside which provide an electrical connection with the top side 98a of piezo film 98. Electrical contacts 242 are connected via an electrical conductor (not shown) in flexible substrate 210 to respective electrical contacts 221 on the patient monitor interface 220.

As can be seen from the above, the present invention provides method and apparatus for monitoring a patient's respiration. Various features and advantages of the invention are set forth in the following claims.

What is claimed is:

1. A respiration sensor comprising:
   a substrate, wherein the substrate includes a sensing region having a base portion, a film ear, and a contact ear; and
   a piezoelectric film mounted on the substrate so that force applied to the sensing region in response to respiration generates a charge on the piezoelectric film.

2. The respiration sensor of claim 1 wherein the substrate includes a connector portion and conductors on the connector portion.

3. The respiration sensor of claim 1 wherein the piezoelectric film is mounted on the film ear.

4. The respiration sensor of claim 1 wherein the base portion includes a base ring mounted on the base portion and foam mounted within the base ring on the base portion.

5. The respiration sensor of claim 1 wherein the contact ear is folded over the base portion and the film ear is folded over the contact ear providing a layered disposition of base portion, contact ear and film ear and wherein the base portion, contact ear and film ear are bonded together using electrically conductive adhesive.

6. The respiration sensor of claim 1 wherein the first piezoelectric film is mounted on the substrate adjacent the first sensing region, and the substrate further includes a second sensing region and a second piezoelectric film is mounted on the substrate adjacent the second sensing region.

7. The respiration sensor of claim 6 wherein the substrate includes a center connection portion connecting the first and second sensing regions.

8. The respiration sensor of claim 7 wherein the connecting portion includes a patient monitor interface.

9. The respiration sensor of claim 1 wherein the force is an acoustical vibration generated by a patient during respiration.

10. The respiration sensor of claim 1 wherein the piezoelectric film has a trapezoidal shape.

11. A respiration sensor comprising:
    a substrate having a first sensing region and a second sensing region, wherein at least one of the first and second sensing regions has a trapezoidal shape;
    a first piezoelectric film mounted on the substrate adjacent the first sensing region so that force applied to the first sensing region in response to respiration generates a charge on the first piezoelectric film; and
    a second piezoelectric film mounted on the substrate adjacent the second sensing region so that force applied to the second sensing region in response to respiration generates a charge on the second piezoelectric film.

12. A patient monitoring apparatus comprising:
    a flexible substrate including a backing layer and a circuit layer having exposed metal contacts, said flexible substrate including:
       a first sensing region having:
          a rigid base ring mounted on the substrate;
          a convex foam material layer mounted on the substrate within the base ring;
          a contact ear connected to the flexible substrate via substrate hinges and being folded over at the hinges so as to rest on the rigid base ring; and a film ear connected to the flexible substrate via substrate hinges and being folded over at the hinges so as to rest on the contact ear, the film ear including a first piezoelectric film layer mounted on the film ear;
       a second sensing region including:
          a rigid base ring mounted on the substrate;
          a convex foam material layer mounted on the substrate within the base ring;
          a contact ear connected to the flexible substrate via substrate hinges and being folded over at the hinges so as to rest on the rigid base ring; and a film ear connected to the flexible substrate via substrate hinges and being folded over at the hinges so as to rest on the contact ear, the film ear including a first piezoelectric film layer mounted on the film ear;
       a patient monitor interface connecting the first and second sensing regions and having electrically conductive contacts for providing an electrical connection between the piezoelectric films and a patient monitor.

13. The respiration sensor of claim 12 wherein the piezoelectric films have a trapezoidal shape.

14. A patient monitor comprising:
    a piezoelectric signal acquisition unit; and
    a respiration sensor connected to the signal acquisition unit, wherein the respiration sensor includes a sensing region having:
       a base portion;
       a film ear; and
       a contact ear.

15. The patient monitor of claim 14 wherein the respiration sensor includes a connecting portion having electrical conductors mounted on the connecting portion.

16. The patient monitor of claim 14 wherein the respiration sensor includes a piezoelectric film configured and arranged to detect acoustical vibrations generated during respiration.

17. The patient monitor of claim 14 wherein the respiration sensor includes piezoelectric film mounted on the film ear.

18. The patient monitor of claim 14 wherein the base portion includes a base ring mounted on the base portion and foam mounted within the base ring on the base portion.

19. The patient monitor of claim 14 wherein the contact ear of said respiration sensor is folded over said base portion and said film ear is folded over said contact ear providing a layered disposition of base portion, contact ear and film ear.

20. The patient monitor of claim 19 wherein the base portion, contact ear and film ear are bonded together using electrically conductive adhesive.

21. The patient monitor of claim 14 including a second respiration sensor having a second sensing region and a second piezoelectric film mounted on the second sensing region.

22. The patient monitor of claim 14 including:
an amplifier for amplifying the signal produced by the sensor;
a signal processor for measuring variations of the signal and converting the variations into a value corresponding to a physiological characteristic; and
a display for displaying said value.

23. The patient monitor of claim 14 including an adaptive noise canceling filter for removing non-respiratory acoustic vibrations.

24. The patient monitor of claim 23 wherein the respiration sensor generates a noise reference signal for use by the adaptive noise canceling filter.

25. The patient monitor of claim 14 wherein the respiration sensor includes a wireless transmitter to transmit the signal to the signal acquisition unit.

26. The patient monitor of claim 14 wherein the respiration sensor is operatively coupled to the signal acquisition unit via a cable.

27. A patient monitor comprising:
a piezoelectric signal acquisition unit; and
a respiration sensor connected to the signal acquisition unit, wherein the respiration sensor includes a piezoelectric film and a foam material with a convex radius for transforming acoustical vibrations perpendicular to the piezoelectric film into longitudinal acoustical vibrations.

28. A method of monitoring the respiration of a patient, said method comprising the acts of:
placing a piezoelectric sensor on the patient, wherein the piezoelectric sensor includes a piezoelectric film and a foam material with a convex radius for transforming acoustical vibrations perpendicular to the piezoelectric film into longitudinal acoustical vibrations;
monitoring acoustical vibrations generated by respiration of the patient; and
providing a value correlating to respiratory activity of the patient based on the acoustical vibrations.

29. The method of claim 28 including the additional act of removing non-respiratory acoustical vibrations using an adaptive noise cancellation filter.

30. The method of claim 29 wherein the additional act of removing nonrespiratory acoustical vibrations using an adaptive noise cancellation filter includes independently sampling noise reference signals and using a computer processor containing an adaptive noise cancellation algorithm to minimize mechanically coupled interference from the sensor.

31. A method of diagnosing respiratory conditions in a patient, said method comprising the acts of:
placing a piezoelectric sensor on the patient, wherein the piezoelectric sensor includes a piezoelectric film and a foam material with a convex radius for transforming acoustical vibrations perpendicular to the piezoelectric film into longitudinal acoustical vibrations;
monitoring acoustical vibrations generated by respiration of the patient using the piezoelectric sensor;
generating a value correlating to respiratory activity of said patient based on the acoustical vibrations; and
comparing the value correlating to the respiratory activity of the patient with known values corresponding to known respiratory conditions.

32. The method of claim 31 wherein the method is achieved using a computer processor to monitor acoustical respiratory data received by the sensor, using a computer processor to compare the data from the patient to known values corresponding to known respiratory conditions thereby predicting the presence of respiratory conditions associated with the existence of specific acoustical respiratory data.

* * * * *